(12) United States Patent
Omori (10) Patent No.: US 8,398,382 B2
(45) Date of Patent: Mar. 19, 2013

(54) TURBO TYPE BLOOD PUMP

(75) Inventor: Masayoshi Omori, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 633 days.

(21) Appl. No.: 12/524,939

(22) PCT Filed: Jan. 24, 2008

(86) PCT No.: PCT/JP2008/050999
§ 371 (c)(1),
(2), (4) Date: Jul. 29, 2009

(87) PCT Pub. No.: WO2008/093594
PCT Pub. Date: Aug. 7, 2008

(65) Prior Publication Data
US 2009/0326649 A1 Dec. 31, 2009

(30) Foreign Application Priority Data

Jan. 30, 2007 (JP) .................................. 2007-019698

(51) Int. Cl.
*F04D 7/02* (2006.01)

(52) U.S. Cl. ................... 417/420; 417/423.1; 417/423.9; 417/423.12

(58) Field of Classification Search ................... 417/420, 417/423.1, 423.9, 423.12; 415/206
See application file for complete search history.

(56) References Cited

U.S. PATENT DOCUMENTS

| | | | |
|---|---|---|---|
| 3,220,638 A | * | 11/1965 | Petersen ........................ 417/368 |
| 5,575,630 A | | 11/1996 | Nakazawa et al. |
| 2004/0091354 A1 | * | 5/2004 | Araki et al. .................... 415/206 |

FOREIGN PATENT DOCUMENTS

| | | |
|---|---|---|
| JP | 2-76196 U | 6/1990 |
| JP | 4-224760 A | 8/1992 |
| JP | 2002-85554 A | 3/2002 |
| JP | 2006-218010 A | 8/2006 |

* cited by examiner

*Primary Examiner* — Charles Freay
*Assistant Examiner* — Christopher Bobish
(74) *Attorney, Agent, or Firm* — Hamre, Schumann, Mueller & Larson, P.C.

(57) ABSTRACT

An impeller 22 includes a rotating shaft 7 supported rotatably by an upper bearing 9 and a lower bearing 20 at upper and lower ends, a plurality of vanes 6, an arm 18 coupling an inner circumferential side of the vanes to the rotating shaft, an annular coupling portion 8 coupled to an outer circumferential side of each vane, and a driven magnet portion 12 placed in a lower portion of the annular coupling portion. A drive magnet portion 16 provided at a rotor 13 and a driven magnet portion 12 are opposed to each other with a bottom wall of the housing interposed therebetween, and rotation of the rotor is transmitted to the impeller through magnetic coupling. A blockade member 23 is placed below the vanes and blocks a space in a region spreading between the rotating shaft and the annular coupling portion while leaving an opening 14 at least around the rotating shaft. In a configuration in which the rotating shaft of the impeller is supported by the upper and lower bearings and a lower portion of each outer circumferential edge of the vanes is coupled to the annular coupling portion, the formation of a blood clot in the vicinity of the lower bearing can be suppressed.

4 Claims, 5 Drawing Sheets

TURBO TYPE BLOOD PUMP

TECHNICAL FIELD

The present invention relates to a blood pump for transporting blood, and in particular, to a turbo type blood pump that subjects blood to a centrifugal force by the rotation of an impeller to allow the blood to flow.

BACKGROUND ART

Blood pumps are indispensable for conducting extracorporeal blood circulation in an artificial heart and lung apparatus and the like. A turbo type blood pump is known as one of the blood pumps. The turbo type blood pump rotates an impeller in a pump chamber having inlet and outlet ports to generate a differential pressure for sending blood with a centrifugal force.

The turbo type blood pump enables a blood pump to be miniaturized and reduced in weight and cost. Furthermore, the turbo type blood pump is excellent in durability since it is not affected by a tube damage or the like unlike a roller-pump type blood pump; therefore, the turbo type blood pump can be used preferably for continuous operation for a long period of time. Thus, the turbo type blood pump is becoming mainstream as a blood pump for an extracorporeal circulation circuit in an artificial heart and lung apparatus or a cardioassist apparatus after open-heart surgery.

In an exemplary turbo type blood pump described in, for example, Patent Document 1, an impeller has a configuration in which a plurality of vanes are provided radially on a circular conical surface of a conical base. The bottom surface of the base has an area to such a degree as to cover almost the entire bottom surface of a housing, so that a whirlpool does not occur in the vicinity of the base, and hence, there is no problem of hemolysis caused by the whirlpool.

However, a stagnant portion of blood is formed in a gap that is present necessarily between the lower surface of the base and the housing, and the heat generated in the bearing portion of the impeller is accumulated in the stagnant blood. Then, due to the influence of the heat in the stagnant portion combined with the shear force caused by the rotation of the impeller, there arises a problem that hemolysis occurs in the stagnant portion. In order to solve this problem, according to Patent Document 1, a blood circulation hole extending from the upper surface to the lower surface is provided in the base. The blood circulation hole allows the blood in the stagnant portion to pass through the vicinity of the bearing portion to reach the upper surface of the base through the blood circulation hole and to flow toward an outer diameter direction of the vanes smoothly, whereby the effect of preventing stagnation can be obtained.

On the other hand, the turbo type blood pump of Patent Document 1 uses a configuration in which the drive force of the impeller is provided from outside via a housing wall through magnetic coupling. More specifically, a magnet is attached to the lower portion of the conical base of the impeller, and a magnet for driving is placed below the outside of the housing so as to be opposed to the magnet of the impeller. The magnet for driving is rotated by a motor, and the impeller is rotated via the magnet of the impeller through magnetic coupling.

However, the configuration for supporting the impeller rotatably, i.e., the bearing structure is provided only in a lower end portion of the impeller. Furthermore, the bottom surface of the conical base has a size so as to cover almost the entire bottom surface of the housing, so that the drive force provided from outside for rotating the impeller becomes large. Consequently, when an attractive force caused by magnetic coupling for providing a drive force is exerted, the supported state of the impeller is likely to be unstable due to the support structure only in the lower end portion.

Figure 6:
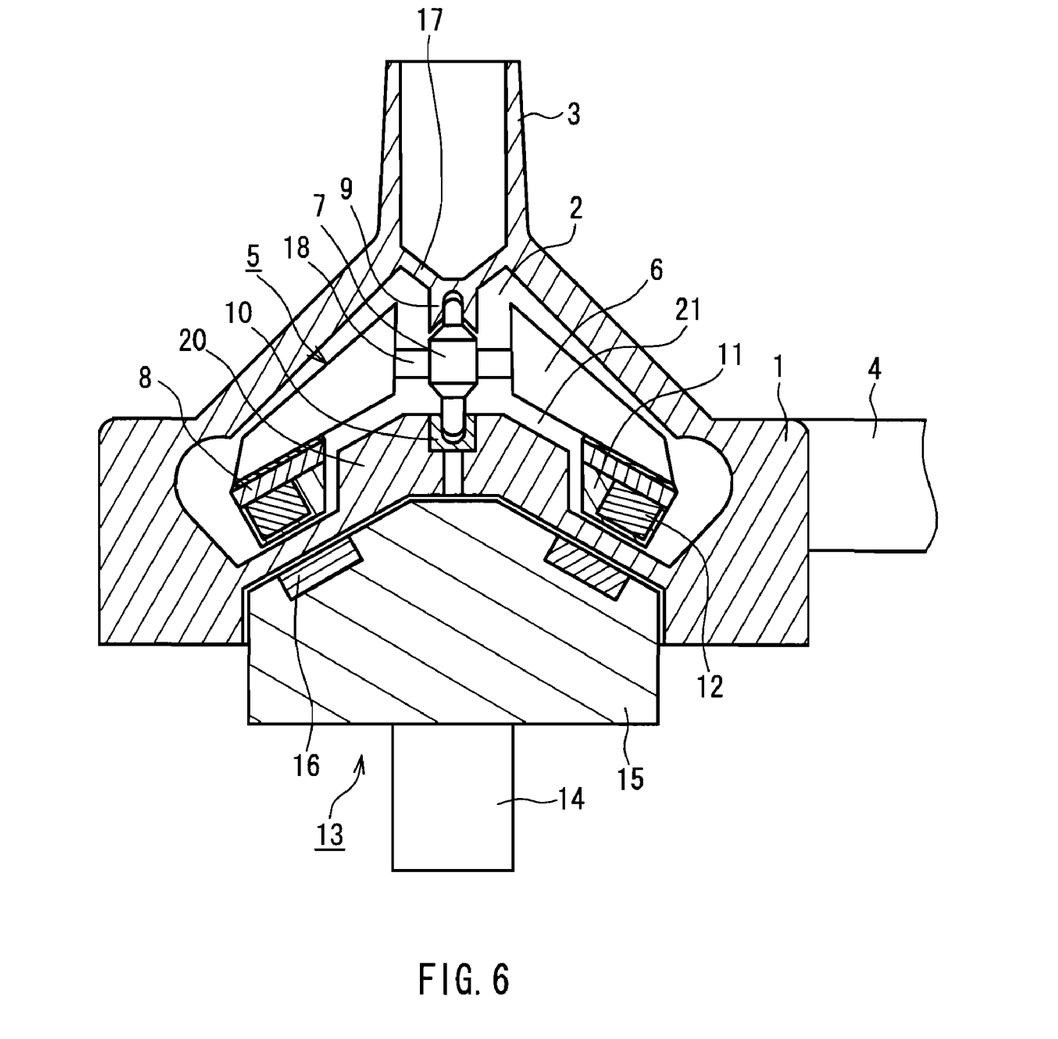
FIG. 6 is a cross-sectional view of a turbo type blood pump in a conventional example.
Figure 7:
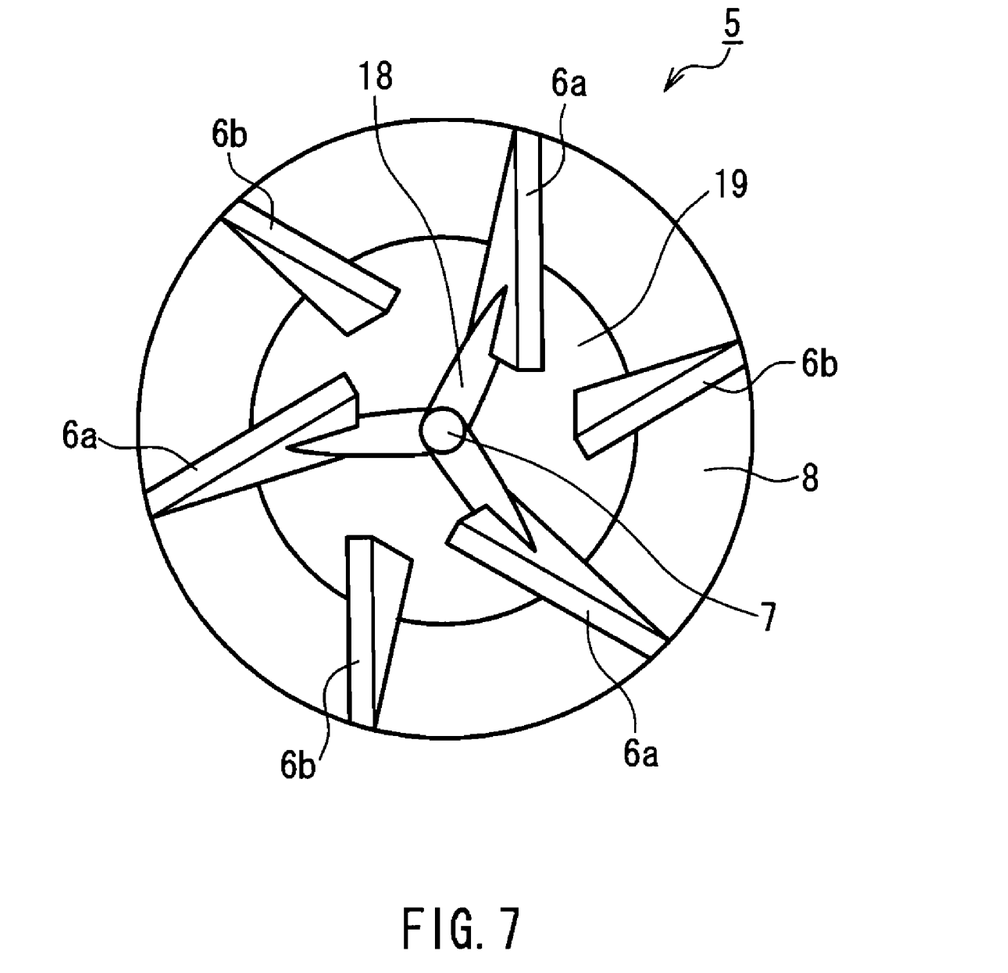
FIG. 7 is a top view of an impeller of the turbo type blood pump in FIG. 6.

In order to solve the problem, the turbo type blood pump described in Patent Document 2 has a horizontal cross-sectional configuration as shown in FIG. 6. In FIG. 6, reference numeral 1 denotes a housing, in which a pump chamber 2 for passing and flowing blood is formed, and an inlet port 3 communicated with the upper portion of the pump chamber 2 and an outlet port 4 communicated with the side portion of the pump chamber 2 are provided. An impeller 5 is placed in the pump chamber 2. FIG. 7 shows a top view of the impeller 5. The impeller 5 includes six vanes 6, a rotating shaft 7, and a ring-shaped annular coupling portion 8.

As shown in FIG. 7, the six vanes 6 include 2 kinds of shapes: large vanes 6a and small vanes 6b, which are placed alternately. A center-side end portion of the large vane 6a is coupled to the rotating shaft 7 via an arm 18, and a circumferential side end portion thereof is connected the annular connecting portion 8. A center-side end portion of the small vane 6b is a free end not coupled to the rotating shaft 7, and only each circumferential end portion thereof is coupled to the annular coupling portion 8. This is because the number of the arms 18 increases when all the vanes 6 are coupled to the rotating shaft 7, interfering with a flow path, which is not preferred. A minimum number of the arms 18 required for transmitting the rotation of the impeller to the rotating shaft 7 may be provided. As is understood from the figure, the impeller 5 has a space 19 in a region inside the annular coupling portion 8, whereby a flow path passing vertically through the vanes 6 is formed.

As shown in FIG. 6, the rotating shaft 7 is supported rotatably by an upper bearing 9 and a lower bearing 10 provided at the housing 1. The annular coupling portion 8 is provided with a magnet case 11, where driven magnets 12 are buried and fixed. The driven magnets 12 have a cylindrical shape, and the six driven magnets 12 are placed at a predetermined interval in the circumferential direction of the annular coupling portion 8. The annular coupling portion 8 and the magnet case 11 form a cylindrical inner circumferential surface.

A rotor 13 is placed below the housing 1. The rotor 13 includes a drive shaft 14 and a substantially cylindrical magnetic coupling portion 15, which are coupled to each other. Although not shown, the drive shaft 14 is supported rotatably, and is coupled to a rotation drive source such as a motor to be rotated. Furthermore, although not shown, the relative positional relationship is kept constant between the rotor 13 and the housing 1. Drive magnets 16 are buried and fixed in an upper surface portion of the magnetic coupling portion 15. The drive magnets 16 have a cylindrical shape, and the six drive magnets 16 are placed at a predetermined interval in a circumferential direction.

The drive magnets 16 are placed so as to be opposed to the driven magnets 12 with a wall of the housing 1 interposed therebetween. Thus, the rotor 13 and the impeller 5 are coupled to each other magnetically, and when the rotor 13 is rotated, the impeller 5 is rotated through magnetic coupling.

Abase 20 having a cylindrical outer circumferential surface, which protrudes upward, i.e., to the inside of the pump chamber 2, is formed at the center in a bottom portion of the housing 1. The base 20 is formed so as to fill the space 19 in a region inside the driven magnets 12 and the annular coupling portion 8 below the impeller 5, which minimizes the volume of the space. This reduces the filling amount of blood in the pump chamber 2.

The upper bearing 9 is placed at a position below the inlet port 3, penetrating the pump chamber 2. Three bearing pillars 17 are provided on the inner surface in a lower end portion of the inlet port 3, and extend diagonally downward to penetrate the pump chamber 2, and the upper bearing 9 is supported by the tip end of the bearing pillars 17 in the center portion of the flow path cross-section of the inlet port 3. The lower bearing 10 is provided at the center in an upper surface portion of the base 20.

In the turbo type blood pump with the above configuration, the impeller 5 is supported vertically by the upper bearing 9 and the lower bearing 10. Therefore, the supported state of the impeller 5 is stable, whereby the stable function of supplying blood can be obtained. Furthermore, the annular coupling portion 8 does not have a size covering the entire bottom surface of the housing 1 as in the conical base in Patent Document 1, and the impeller 5 has a space in a region spreading between the rotating shaft 7 and the annular coupling portion 8. Thus, the impeller 5 is light-weight, and a small drive force suffices.

Furthermore, a flow path passing through the vanes vertically is formed in the region spreading between the rotating shaft 7 and the annular coupling portion 8. Therefore, in the same way as in the function of the blood circulation hole in Patent Document 1, the blood in the stagnant portion formed in the lower portion of the impeller 5 passes through the vicinity of the lower bearing 10 to reach the upper portion of the impeller 5 and to flow toward the outer diameter direction of the impeller 5.

Patent Document 1: JP 4(1992)-224760 A
Patent Document 2: JP 2002-85554 A

DISCLOSURE OF INVENTION

Problem to be Solved by the Invention

However, it was found that, in the case of the configuration of the blood pump in the conventional example disclosed in Patent Document 2, a large number of blood clots are formed around the rotating shaft 7, for example, in the vicinity of the lower bearing 10 on the upper surface of the base 20.

As a result of the experiment, it was found that, although the blood in the gap between the impeller 5 and the bottom surface of the housing 1 flows toward the center of the impeller 5, the flow rate of a blood stream decreases in a gap portion 21 inside the annular coupling portion 8, and in particular, a blood stream with a sufficient flow rate is not formed in the vicinity of the lower bearing 10 on the upper surface of the base 20. Therefore, the blood stagnates and heat generated by the lower bearing 10 causes hemolysis as a main factor. Furthermore, due to the above stagnation, a blood clot is likely to be formed in the vicinity of the lower bearing.

An object of the present invention is to provide a turbo type blood pump having a rotating shaft of an impeller supported by upper and lower bearings, with lower portions of outer circumferential edges of vanes being coupled to an annular coupling portion, in which the formation of a blood clot is suppressed in the vicinity of the lower bearing.

Means for Solving Problem

A turbo type blood pump of the present invention includes: a housing having a pump chamber, an inlet port, and an outlet port; an impeller supported rotatably in the pump chamber; and a drive force transmitting element for rotating the impeller. The impeller includes: a rotating shaft supported rotatably by an upper bearing and a lower bearing at upper and lower ends; a plurality of vanes; an arm coupling an inner circumferential side of at least a part of the vanes to the rotating shaft; an annular coupling portion coupled to each outer circumferential side of the vanes; and a driven magnet portion placed in a lower portion of the annular coupling portion. The drive force transmitting element is configured in such a manner that a drive magnet portion placed in an outside lower portion of the housing and provided at a rotatable rotor and the driven magnet portion of the impeller are opposed to each other with a bottom wall of the housing interposed therebetween, and rotation of the rotor is transmitted to the impeller through magnetic coupling.

In order to solve the above problem, the impeller includes a blockade member placed below the vanes in a region spreading between the rotating shaft and the annular coupling portion, and the blockade member blocks a space in the region spreading between the rotating shaft and the annular coupling portion while leaving an opening at least around the rotating shaft.

Effects of the Invention

According to the above configuration, the blood in the gap between the impeller and the bottom surface of the housing flows toward the center of the impeller along the lower surface of the blockade member, and thereafter, rises through the opening of the blockade member. Since an opening area of the blockade member is limited, a blood stream with a sufficient flow rate is formed adjacent to the lower bearing along the rotating shaft, which prevents the stagnation of blood. Thus, according to the configuration of the conventional example, the region where blood stagnates and a blood clot is likely to be formed due to the heat generated by the lower bearing also is ready to be washed away at all times, so that the formation of a blood clot is suppressed. Furthermore, in this site, the above flow of blood suppresses the rise in temperature of blood caused by the heat generated by the lower bearing.

DESCRIPTION OF REFERENCE NUMERALS 1 housing
2 pump chamber
3 inlet port
4 outlet port
5, 22, 25 impeller
6 vane
6a large vane
6b small vane
7 rotating shaft 8 annular coupling portion
9 upper bearing
10 lower bearing
11 magnet case
12 driven magnet
13 rotor
14 driveshaft
15 magnetic coupling portion
16 drive magnet
17 bearing pillar
18 arm
19 space
20 base
21 gap portion
23, 26 blockade member
24 opening
27 circular region
28 radial region

DESCRIPTION OF THE INVENTION

The turbo type blood pump of the present invention can assume aspects varied as follows on the basis of the above configuration.

More specifically, it is preferred that a base having a cylindrical outer circumferential surface protruding upward is formed at a center in a bottom portion of the housing so as to correspond to a space in a region of a lower portion of the impeller surrounded by a cylindrical inner circumferential surface that is formed by the annular coupling portion and the driven magnet portion, and the base is provided with the lower bearing.

It is preferred that an opening of the blockade member has a circular shape concentric with the rotating shaft, and when a diameter of the opening of the blockade member is defined as d and a diameter of the cylindrical outer circumferential surface of the base is defined as D, the diameter d of the opening is set in a range of $0.12D \leq d \leq 0.3D$. More preferably, the diameter d of the opening is set in a range of $0.12D \leq d \leq 0.225D$.

Furthermore, the opening of the blockade member may include a plurality of radial regions extending radially from a circular region concentric to the rotating shaft.

Hereinafter, a turbo type blood pump in embodiments of the present invention will be described with reference to the drawings.

Embodiment 1

The basic configuration of a turbo type blood pump in Embodiment 1 of the present invention is the same as that in the conventional example shown in FIGS. 6 and 7. Thus, the same components as those shown in FIGS. 6 and 7 are denoted with the same reference numerals as those therein, and the repeated descriptions thereof will be omitted.

Figure 1:
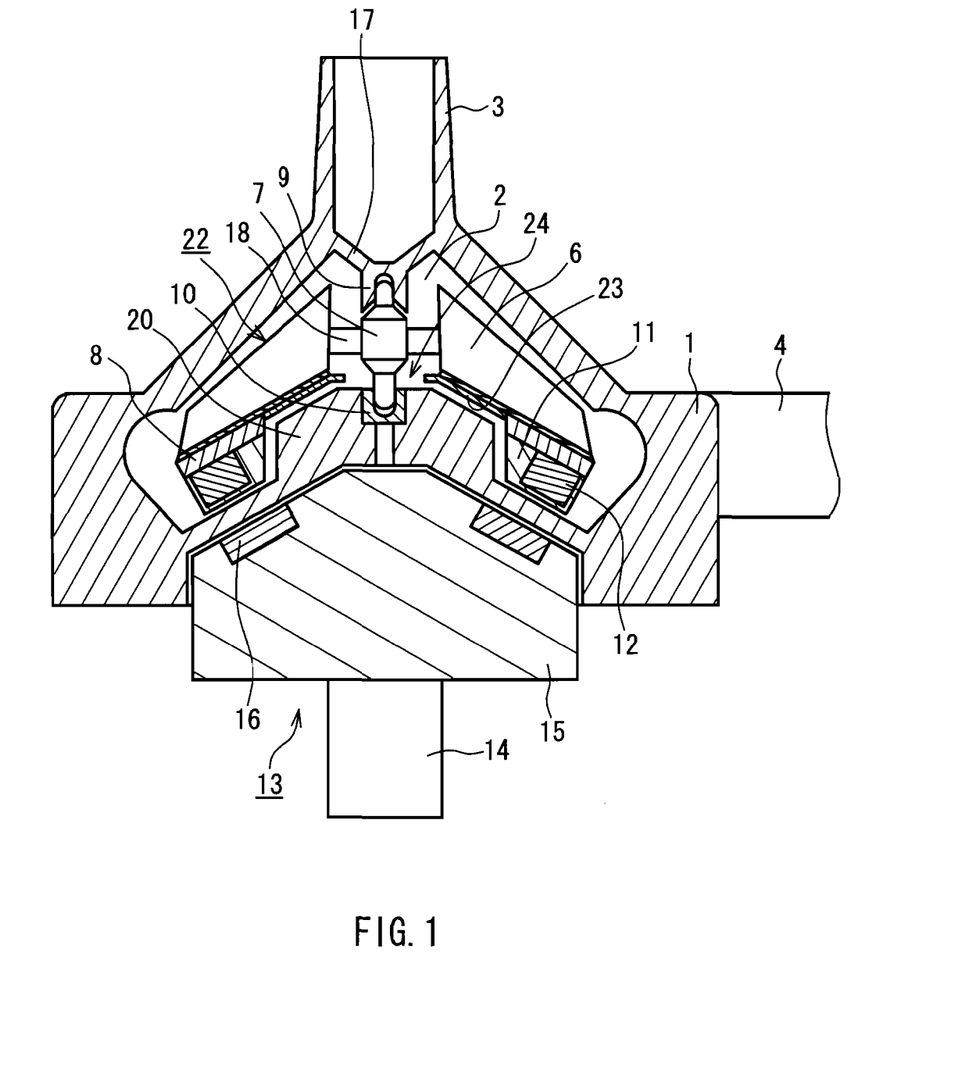
FIG. 1 is a cross-sectional view of a turbo type blood pump in Embodiment 1 of the present invention.

FIG. 1 is a cross-sectional view showing a turbo type blood pump in the present embodiment. A housing 1 forms a pump chamber 2. An inlet port 3 is provided in an upper portion of the pump chamber 2 and an outlet port 4 is provided in a side portion of the pump chamber 2. An impeller 22 has a configuration in which vanes 6 are attached to a rotating shaft 7 via arms 18, and each circumferential edge of the vanes 6 is coupled to an annular coupling portion 8.

Figure 2:
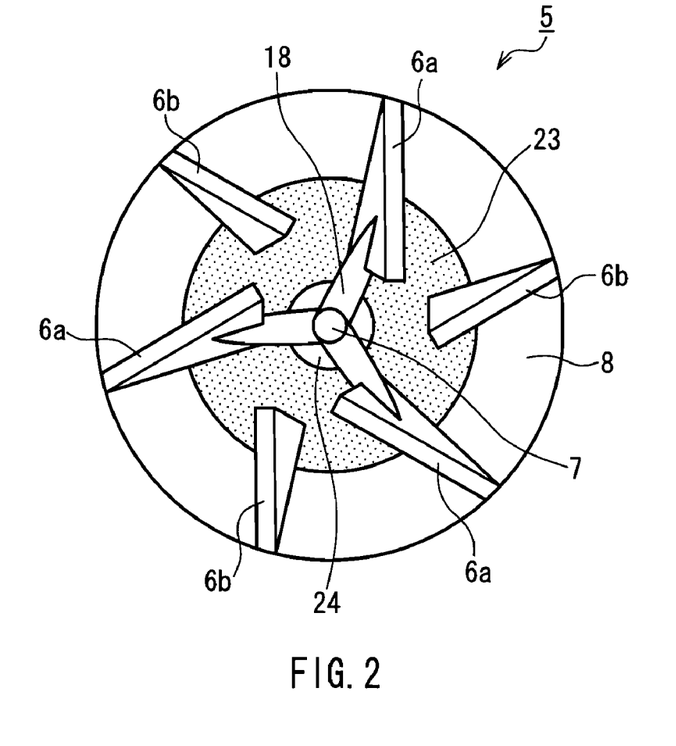
FIG. 2 is a top view of an impeller of the turbo type blood pump in FIG. 1.
Figure 3:
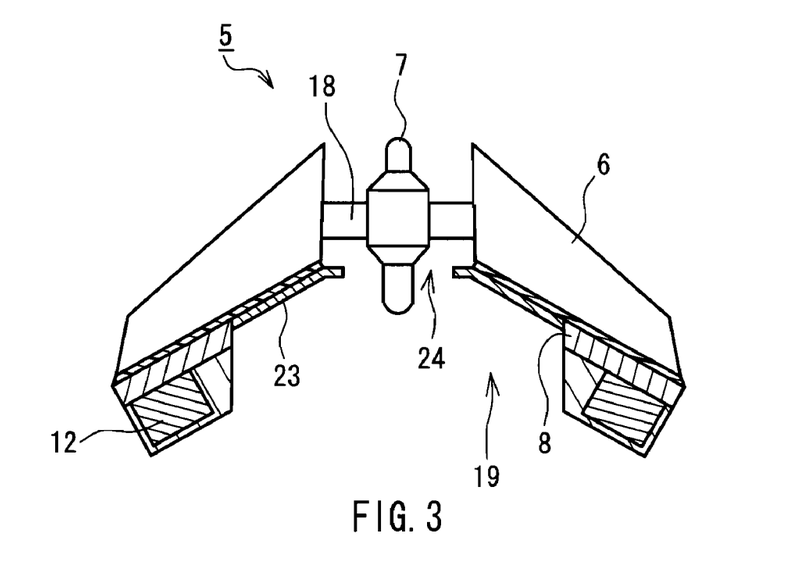
FIG. 3 is a cross-sectional view of the impeller.

FIG. 2 shows a top view of the impeller 22, and FIG. 3 shows a cross-sectional view thereof. As shown in FIG. 2, the six vanes 6 are composed of large vanes 6a and small vanes 6b, which are placed alternately. Each center-side end portion of the large vanes 6a is coupled to the rotating shaft 7 via the arm 18, and each center-side end portion of the small vanes 6b is a free end not coupled to the rotating shaft 7 and only each circumferential end portion thereof is coupled to the annular coupling portion 8.

As shown in FIG. 1, the rotating shaft 7 is supported rotatably by an upper bearing 9 and a lower bearing 10 provided at the housing 1. The annular coupling portion 8 is provided with a magnet case 11, where driven magnets 12 are buried and fixed. A drive shaft 14 and a rotor 13 having a substantially cylindrical magnetic coupling portion 15, which are coupled to each other, are placed below the housing 1. Drive magnets 16 are buried and fixed in an upper surface portion of the magnetic coupling portion 15. The drive magnets 16 are placed so as to be opposed to the driven magnets 12 with a wall of the housing 1 interposed therebetween, and the rotor 13 and the impeller 22 are formed so as to be coupled magnetically.

A surface of the annular coupling portion 8, on which the driven magnets 12 are set, is an inclined surface that is not orthogonal to the rotating shaft 7 and has a predetermined angle. Similarly, an upper surface of the magnetic coupling portion 15, on which the drive magnets 16 are set, is an inclined surface. Thus, the driven magnets 12 and the drive magnets 16 form magnetic coupling on a surface inclined with respect to the rotating shaft of the impeller 22, whereby the magnetic attractive force acting on an area between the impeller 22 and the rotor 13 is generated in a direction inclined with respect to the rotating shaft of the impeller 22. Consequently, the downward load with respect to the lower bearing 10 is reduced. Thus, the friction of the lower bearing 10 is alleviated, and the strength of magnetic coupling can be made sufficiently large.

As shown in FIG. 3, the impeller 22 has a space 19 in a region inside the annular coupling portion 8. An inner circumferential surface of the annular coupling portion 8 and the magnetic case 11 forms a cylindrical surface. As shown in FIG. 1, a base 20 having a cylindrical outer circumferential surface, which protrudes upward, i.e., to the inside of the pump chamber 2, is formed at the center in a bottom portion of the housing 1. The base 20 is formed so as to fill the space 19 in the region inside the driven magnets 12 and the annular coupling portion 8 in the lower portion of the impeller 22, which minimizes the volume of the space.

The upper bearing 9 is supported by the tip end of three bearing pillars 17 provided on the inner surface in a lower end portion of the inlet port 3. The lower bearing 10 is provided at the center in the upper surface portion of the base 20.

As clearly shown in FIGS. 2 and 3, the impeller 11 has a blockade member 23 placed below the vanes 6 in a region spreading between the rotating shaft 7 and the annular coupling portion 8. The blockade member 23 blocks a flow path passing through the vanes 6 from the space in the region spreading between the rotating shaft 7 and the annular coupling portion 8 while leaving a part of an opening 24 around the rotating shaft 7. By providing the blockade member 23, the formation of a blood clot around the rotating shaft 7, for example, in the vicinity of the lower bearing 10 on the upper surface of the base 20 can be suppressed as described below.

More specifically, by providing the blockade member 23, the blood in the gap between the impeller 22 and the bottom surface of the housing 1 flows toward the center of the impeller 5 along the lower surface of the blockade member 23, and thereafter, rises through the opening 24 of the blockade member 23. At this time, since the area of the opening 24 is limited, a blood stream at a sufficient flow rate is formed adjacent to the lower bearing 10 along the rotating shaft 7, which prevents the stagnation of blood. Thus, it is considered that the region where blood stagnates to form a blood clot according to the configuration in the conventional example also is ready to be washed away at all times, and hence, the formation of a blood clot is suppressed.

Figure 4:
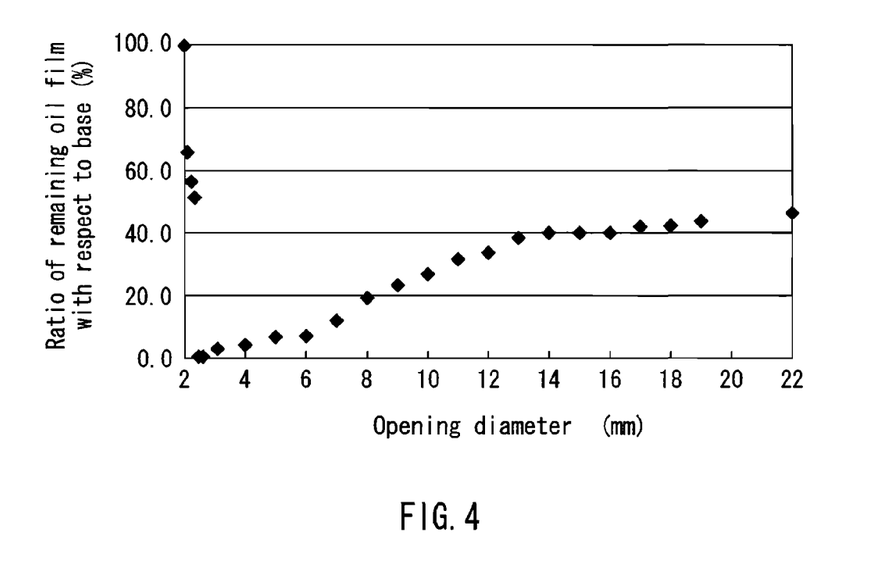
FIG. 4 is a diagram showing experimental results obtained by conducting an experiment regarding the effect of suppressing the formation of a blood clot in the turbo type blood pump in FIG. 1.

FIG. 4 shows the experimental results for confirming the results obtained by the blockade member 23. As a test liquid for evaluation of the formation of a blood clot, a liquid in which oil paint and oil were mixed in a weight ratio of 6:4 was used. The test liquid was circulated by pump driving while the diameter of the opening 24 of the blockade member 23 is changed in the configuration of the turbo type blood pump shown in FIG. 1, whereby the size of an oil film formed on the upper surface of the base 20 was inspected. The pump flow rate was 2.0 L/min., the rotation number was 4000 min−1, and the circulation time was 2 minutes.

In the graph shown in FIG. 4, a horizontal axis represents a diameter d of the opening 24 of the blockade member 23. A vertical axis represents a ratio (%) of the diameter of the formed oil film remaining oil film) with respect to the diameter of the base 20. The diameter of the base 20 represents a diameter D (=20 mm) of a cylindrical surface of the base 20. The diameter of the rotating shaft 7 is 2 mm and the diameter of the inner circumferential surface of the annular coupling portion 8 is 22 mm. Thus, the diameter d of the opening 24 was changed in a range of 2 mm to 22 mm.

Along with the decrease in the diameter d of the opening 24 from 22 mm (without the blockade member 23), the ratio of the remaining oil film starts decreasing from the vicinity of 13 mm. When the diameter d reaches 6 mm, the effect of reducing the remaining oil film obtained by decreasing the diameter d becomes mild. The effect of decreasing the remaining oil film was largest when the diameter d was in a range of 2.4 mm to 4.5 mm. When the diameter d was smaller than 2.4 mm, the ratio of the remaining oil film increased. This is because the flow path of blood becomes too small.

As described above, the diameter d of the opening 24 is optimally in a range of 2.4 mm to 4.5 mm in order to suppress the formation of a blood clot. On the other hand, even when the diameter d of the opening 24 is set to be larger than the above optimum range, i.e., more than 4.5 mm to 6 mm, considering the outher conditions, the effect of suppressing the formation of a blood clot is obtained sufficiently for practical applications. Although the appropriate range of the diameter d of the opening 24 varies slightly depending upon the size of the turbo type blood pump, the desired effects can be obtained by setting the diameter d in a standardized range as follows in the case of a turbo type blood pump in a range used ordinarily.

More specifically, the diameter d of the opening 24 should be set in a range of $0.12D \leqq d \leqq 0.3D$, preferably in a range of $0.12D \leqq d \leqq 0.225D$ with respect to the diameter D of the cylindrical surface of the base 20.

Embodiment 2

A turbo type blood pump in Embodiment 2 of the present invention will be described with reference to the top view of the impeller 25 shown in FIG. 5. The configuration of the turbo type blood pump in the present embodiment is substantially the same as that in Embodiment 1.

Figure 5:
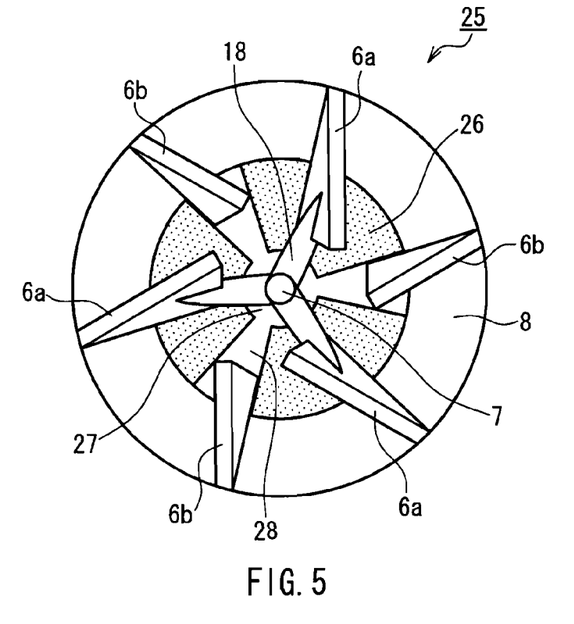
FIG. 5 is a top view showing an impeller of a turbo type blood pump in Embodiment 2 of the present invention.

In the present embodiment, as shown in FIG. 5, only the shape of the blockade member 26 of the impeller 25 is different from that in Embodiment 1. More specifically, the opening of the blockade member 26 has a circular region 27 concentric to the rotating shaft 7, and further includes a plurality of radial regions 28 extending radially from the circular region 27.

Even if the opening of the blockade member 26 is formed in such a shape, the effect of suppressing the formation of a blood clot by the circular region 27 can be obtained to a sufficiently degree for practical applications. In addition, the efficiency of priming can be enhanced by providing the radial regions 28. If the opening ratio of the radial regions 28 is set to be too large, the effect of suppressing the formation of a blood clot is reduced. Thus, it is desirable to determine the opening ratio of the radial regions 28, considering the balance of both the effects in accordance with the shape and size of each portion.

INDUSTRIAL APPLICABILITY

In a turbo type blood pump of the present invention, the formation of a blood clot is suppressed in the vicinity of a lower bearing in a configuration in which an impeller is supported by upper and lower bearings, and a lower portion of outer circumferential edges of vanes are coupled to an annular coupling portion, and thus, the turbo type blood pump is preferred as a blood pump for conducting extracorporeal blood circulation in an artificial heart and lung apparatus and the like.

The invention claimed is:

1. A turbo type blood pump, comprising:
   a housing having a pump chamber, an inlet port, and an outlet port;
   an impeller supported rotatably in the pump chamber; and
   a drive force transmitting element for rotating the impeller,
   the impeller including: a rotating shaft supported rotatably by an upper bearing and a lower bearing at upper and lower ends;
   a plurality of vanes;
   an arm coupling an inner circumferential side of at least a part of the vanes to the rotating shaft;
   an annular coupling portion coupled to each outer circumferential side of the vanes; and
   a driven magnet portion placed in a lower portion of the annular coupling portion,
   the drive force transmitting element being configured in such a manner that a drive magnet portion provided at a rotatable rotor positioned in an outside lower portion of the housing and the driven magnet portion of the impeller are opposed to each other with a bottom wall of the housing interposed therebetween, whereby rotation of the rotor is transmitted to the impeller through magnetic coupling,
   wherein a base having a cylindrical outer circumferential surface protruding upward is formed at a center in a bottom portion of the housing so as to correspond to a space in a region of a lower portion of the impeller surrounded by a cylindrical inner circumferential surface that is formed by the annular coupling portion and the driven magnet portion,
   the lower bearing is provided at the base,
   the impeller includes a blockade member extending inwardly from an inner edge of the annular coupling portion over the upper surface of the base, so as to be interposed between a lower surface of the vanes and an upper surface of the base in a region spreading between the rotating shaft and the annular coupling portion, and
   the blockade member is a single piece structure and blocks a space in the region spreading between the rotating shaft and the inner edge of the annular coupling portion while leaving only an opening for a part of the space around the rotating shaft above the base.

2. The turbo type blood pump according to claim 1, wherein an opening of the blockade member has a circular shape concentric with the rotating shaft, and when a diameter of the opening of the blockade member is defined as d and a diameter of the cylindrical outer circumferential surface of the base is defined as D, the diameter d of the opening is set in a range of $0.12D \leqq d \leqq 0.3D$.

3. The turbo type blood pump according to claim 2, wherein the diameter d of the opening is set in a range of $0.12D \leqq d \leqq 0.225D$.

4. The turbo type blood pump according to claim 2, wherein the opening of the blockade member includes a plurality of radial regions extending radially from a circular region concentric to the rotating shaft.

* * * * *